(12) United States Patent
Zang

(10) Patent No.: US 7,695,713 B2
(45) Date of Patent: Apr. 13, 2010

(54) ISOLATION AND IDENTIFICATION OF T CELLS

(75) Inventor: Jingwu Z. Zang, Shanghai (CN)

(73) Assignee: Baylor College of Medicine, Houston, TX (US)

( * ) Notice: Subject to any disclaimer, the term of this patent is extended or adjusted under 35 U.S.C. 154(b) by 744 days.

(21) Appl. No.: 10/524,300

(22) PCT Filed: Aug. 6, 2003

(86) PCT No.: PCT/US03/24548

§ 371 (c)(1), (2), (4) Date: Aug. 29, 2005

(87) PCT Pub. No.: WO2004/015070

PCT Pub. Date: Feb. 19, 2004

(65) Prior Publication Data

US 2006/0105336 A1    May 18, 2006

Related U.S. Application Data

(60) Provisional application No. 60/402,521, filed on Aug. 8, 2002.

(51) Int. Cl.
*A61K 39/38*   (2006.01)
*C12N 5/07*    (2006.01)

(52) U.S. Cl. .................... 424/93.71; 435/325; 435/373; 435/375; 435/377

(58) Field of Classification Search .................. None
See application file for complete search history.

(56) References Cited

U.S. PATENT DOCUMENTS

| | | | |
|---|---|---|---|
| 4,550,086 A | 10/1985 | Reinherz et al. |
| 4,608,365 A | 8/1986 | Engel |
| 4,677,061 A | 6/1987 | Rose et al. |
| 4,897,389 A | 1/1990 | Aroonsakul |
| 4,898,856 A | 2/1990 | Aroonsakul |
| 4,898,857 A | 2/1990 | Aroonsakul |
| 4,902,680 A | 2/1990 | Aroonsakul |
| 4,996,194 A | 2/1991 | Cohen et al. |
| 5,039,660 A | 8/1991 | Leonard et al. |
| 5,112,810 A | 5/1992 | Nagai et al. |
| 5,211,952 A | 5/1993 | Spicer et al. |
| 5,242,687 A | 9/1993 | Tykocinski |
| 5,298,396 A | 3/1994 | Kotzin et al. |
| 5,340,584 A | 8/1994 | Spicer et al. |
| 5,445,939 A | 8/1995 | Anderson |
| 5,480,895 A | 1/1996 | Friedman et al. |
| 5,494,899 A | 2/1996 | Kincade et al. |
| 5,545,716 A | 8/1996 | Johnson et al. |
| 5,552,300 A | 9/1996 | Makrides et al. |
| 5,554,595 A | 9/1996 | Kincade et al. |
| 5,569,585 A | 10/1996 | Goodwin et al. |
| 5,614,192 A | 3/1997 | Vandenbark |
| 5,643,572 A | 7/1997 | Byers et al. |
| 5,656,446 A | 8/1997 | Anderson |
| 5,668,117 A | 9/1997 | Shapiro |
| 5,674,487 A | 10/1997 | Smith et al. |
| 5,716,946 A | 2/1998 | DeLuca et al. |
| 5,723,503 A | 3/1998 | Smith et al. |
| 5,750,356 A | 5/1998 | Spack et al. |
| 5,766,920 A | 6/1998 | Babbitt et al. |
| 5,776,459 A | 7/1998 | Vandenbark |
| 5,776,708 A | 7/1998 | Kotzin et al. |
| 5,817,622 A | 10/1998 | Johnson et al. |
| 5,837,246 A | 11/1998 | Howell et al. |
| 5,843,689 A | 12/1998 | Anderson et al. |
| 5,849,886 A | 12/1998 | Maatta et al. |
| 5,858,364 A | 1/1999 | Weiner et al. |
| 5,861,164 A | 1/1999 | Howell et al. |
| 5,869,057 A | 2/1999 | Rock |
| 5,874,531 A | 2/1999 | Strominger et al. |
| 6,007,815 A | 12/1999 | Howell et al. |
| 6,033,661 A | 3/2000 | Smith et al. |
| 6,043,236 A | 3/2000 | Brattsand et al. |
| 6,054,292 A | 4/2000 | Hillman et al. |
| 6,083,503 A | 7/2000 | Leonard |
| 6,083,521 A | 7/2000 | Acemoglu et al. |
| 6,090,387 A | 7/2000 | Howell et al. |

(Continued)

FOREIGN PATENT DOCUMENTS

| | | |
|---|---|---|
| WO | WO 91/15225 | 10/1991 |
| WO | WO 94/26876 | 11/1994 |
| WO | WO 97/35879 A1 * | 10/1997 |
| WO | WO 99/13904 | 3/1999 |
| WO | WO 00/14116 | 3/2000 |
| WO | PCT/US00/22988 | 8/2000 |
| WO | WO 03/024393 | 3/2003 |

OTHER PUBLICATIONS

The Merck Manual. 16th Edition, 1992, Merck & Co., Inc., Rahway, N.J., p. 21.*

(Continued)

*Primary Examiner*—Ram R Shukla
*Assistant Examiner*—Marianne DiBrino
(74) *Attorney, Agent, or Firm*—Polsinelli Shughart PC; Teddy C. Scott, Jr.; Paul A. Jenny

(57) ABSTRACT

The present invention relates to improved autologous T cell vaccines and improved methods for their production. The invention is also directed to methods for treating autoimmune diseases such as multiple sclerosis or rheumatoid arthritis using autologous T cell vaccines. The invention is further directed to the diagnosis of T cell associated diseases.

8 Claims, 2 Drawing Sheets

U.S. PATENT DOCUMENTS

| | | | |
|---|---|---|---|
| 6,096,314 | A | 8/2000 | Cohen et al. |
| 6,114,388 | A | 9/2000 | Geffard |
| 6,130,087 | A | 10/2000 | Sruvastava et al. |
| 6,159,470 | A | 12/2000 | Howell et al. |
| 6,187,750 | B1 | 2/2001 | Chien |
| 6,207,147 | B1 | 3/2001 | Hiserodt |
| 6,207,645 | B1 | 3/2001 | Howell et al. |
| 6,218,132 | B1 | 4/2001 | Spack et al. |
| 6,218,166 | B1 | 4/2001 | Ravindranath et al. |
| 6,221,352 | B1 | 4/2001 | Howell et al. |
| 6,303,314 | B1 * | 10/2001 | Zhang ............................ 435/6 |
| 6,489,299 | B2 | 12/2002 | Steinman et al. |
| 6,746,670 | B2 | 6/2004 | Levings et al. |
| 2001/0031253 | A1 | 10/2001 | Gruenberg |
| 2002/0009448 | A1 | 1/2002 | Weiner et al. |
| 2002/0072493 | A1 | 6/2002 | Eisenbach-Schwartz et al. |
| 2003/0091578 | A1 | 5/2003 | Zang |
| 2003/0153073 | A1 | 8/2003 | Rogers et al. |

OTHER PUBLICATIONS

Encyclopedia Brittanica Online. www.search.eb.com/eb/print?eu=76559, 2004, 2 pages.*

Minohara et al (Tissue Antigens, 2001, 57: 447-456).*

Tourdot et al (J. Immunol. 1997, 159: 2391-2398).*

Zhang (Crit. Rev. Immunol. 2001, 21: 41-55).*

Tejeda-Simon et al (International Immunol. 2000, 12(12): 1641-1650).*

Correale et al (J. Neuroimmunol. 107: 130-139, 2000).*

Hermans, G., et al., "Cytokine Profile of Myelin Basic Protein-Reactive T Cells in Multiple Sclerosis and Healthy Individuals," Annals of Neurology, vol. 42, No. 1, pp. 18-27 (Jul. 1997).

Rohowsky-Kochan, C., et al., "Cytokine Secretion Profile of Myelin Basic Protein-Specific T Cells in Multiple Sclerosis," Multiple Sclerosis, vol. 6, pp. 69-77 (2000).

Tejada-Simon, M., et al., "Reactivity Pattern and Cytokine Profile of T Cells Primed by Myelin Peptides in Multiple Sclerosis and Healthy Individuals," Eur. Journal Immunol., vol. 31, pp. 907-917 (2001).

Jingwu Zang et al., MHC-Restricted Depletion of Human Myelin Basic Protein-Reactive T Cells by T Cell Vaccination, Science, 1993; 261:1451-1454.

Jessee, D., "Notice of Grant Award," for National Institutes of Health Grant No. 1 R01 NS38213-01A1. Awarded to Dr. Leslie P. Weiner on Jul. 30, 1999. Obtained pursuant to Freedom of Information Act.

Weiner, L., Grant Application entitled, "T Cell Vaccine—A Clinical Trial for Progressive MS." National Institutes of Health Grant No. 1 R01 NS38213-01A1. Awarded on Jul. 30, 1999. Obtained pursuant to Freedom of Information Act.

Jessee, D., "Notice of Grant Award," for National Institutes of Health Grant No. 5 R01 NS38213-02. Awarded to Dr. Leslie P. Weiner on Jul. 24, 2000. Obtained pursuant to Freedom of Information Act.

Weiner, L., Grant Application entitled, "T Cell Vaccine—A Clinical Trial for Progressive MS." National Institutes of Health Grant No. 5 R01 NS38213-02. Awarded on Jul. 24, 2000. Obtained pursuant to Freedom of Information Act.

Jessee, D., "Notice of Grant Award," for Naitonal Institutes of Health Grant No. 5 R01 NS38213-03. Awarded to Dr. Leslie P. Weiner on Aug. 5, 2001. Obtained pursuant to Freedom of Information Act.

Weiner, L., Grant Application entitled, "T Cell Vaccine—A Clinical Trial for Progressive MS." National Institutes of Health Grant No. 5 R01 NS38213-03. Awarded on Aug. 5, 2001. Obtained pursuant to Freedom of Information Act.

Bond, K.P., "Notice of Grant Award," for National Institutes of Health Grant No. 5 R01 NS38213-04. Awarded to Dr. Leslie P. Weiner on Aug. 8, 2002. Obtained pursuant to Freedom of Information Act.

Weiner, L., Grant application entitled, "T Cell Vaccine—A Clinical Trial for Progressive MS." National Institutes of Health Grant No. 5 R01 NS38213-04. Awarded on Aug. 8, 2002. Obtained pursuant to Freedom of Information Act.

Bond, K.P., "Notice of Grant Award," for National Institutes of Health Grant No. 5 R01 NS38213-05. Awarded to Dr. Leslie P. Weiner on Sep. 17, 2003. Obtained pursuant to Freedom of Information Act.

Weiner, L., Grant application entitled, "T Cell Vaccine—A Clinical Trial for Progressive MS." National Institutes of Health Grant No. 5 R01 NS38213-05. Awarded on Sep. 17, 2003. Obtained pursuant to Freedom of Information Act.

Bond, K.P., "Notice of Grant Award," for National Institutes of Health Grant No. 5 R01 NS38213-06. Awarded to Dr. Leslie P. Weiner on Jul. 23, 2004. Obtained pursuant to Freedom of Information Act.

Weiner, L., Grant application entitled, "T Cell Vaccine—A Clinical Trial for Progressive MS." National Institutes of Health Grant No. 5 R01 NS38213-06. Awarded on Jul. 23, 2004. Obtained pursuant to Freedom of Information Act.

Bond, K.P., "Notice of Grant Award," for National Institutes of Health Grant No. 5 R01 NS38213-07. Awarded to Dr. Leslie P. Weiner on Aug. 3, 2005. Obtained pursuant to Freedom of Information Act.

Weiner, L., Grant application entitled, "T Cell Vaccine—A Clinical Trial for Progressive MS." National Institutes of Health Grant No. 5 R01 NS38213-07. Awarded on Aug. 3, 2005. Obtained pursuant to Freedom of Information Act.

Zang, CQ. Preferential recognition of TCR hypervariable regions by human anti-idiotypic T cells introduced by T cell vaccination. Journal of Immunology 164:4011-7 (2000).

Hohfield, R. The ups and downs of multiple sclerosis therapeutics. Annals of Neurology 49(3): 281-84 (2001).

Joshi, N. The T-cell response to myelin basic protein in familial multiple sclerosis: diversity of fine specificity, restricting elements, and T-cell receptor usage. Annals of Neurology 34:385-93 (1993).

Tournier-Lasserve, E. Human T-cell response to myelin basic protein in multiple sclerosis patients and healthy subjects. Journal of Neuroscience Research 19:149-56 (1988).

Pette, M. Myelin basic protein-specific T lymphocyte lines from MS patients and healthy individuals. Neurology 40:1770-6 (1990).

Liblau, R. T cell response to myelin basic protein epitopes in multiple sclerosis patients and healthy subjects. Eur J Immunol 21:1391-5 (1991).

Shanmugam, A. In vivo clonal expansion of T lymphocytes specific for an immunodominant N-terminal myelin basic protein epitope in healthy individuals. Journal of Neuroimmunology 59:165-72 (1995).

Hellings, N. T-cell reactivity to multiple myelin antigens in multiple sclerosis patients and healthy controls. Journal of Neuroscience Research 63: 290-302 (2001).

Martin, R. Diversity in fine specificity and T cell receptor usage of the human CD4+ cytotoxic T cell response specific for the immunodominant myelin basic protein peptide 87-106. Journal of Immunology 148:1359-66 (1992).

Pette, M. Myelin autoreactivity in multiple sclerosis: recognition of myelin basic protein in the context of HLA-DRA2 products by T lymphocytes of multiple sclerosis patients and healthy donors. Proc Natl Acad Sci USA 87:7968-72 (1990).

Blevins, G. Future imunotherapies in multiple sclerosis. Semin Neurol 23(2):147-58 (2003).

Feldman, M. Design of effective immunotherapy for human autoimmunity. Nature 435:612-9 (2005).

Hong,J. Ex vivo detection of myelin basic protein-reactive T cells in multiple sclerosis and controls using specific TCR oligonucleotide probes. Eur J Immunol 34:870-81 (2004).

Martin, R. Fine specificity and HLA restriction of myelin basic protein-specific cytotoxic T cell lines from multiple sclerosis patients and healthy individuals. Journal of Immunology 145:540-8 (1990).

Hellings, N. Longitudinal study of antimyelin T cell reactivity in relapsing remitting multiple sclerosis association with clinical and MRI activity. J Neuroimmunol 126(1-2):143-60 (2002).

Sospreda, M. Immunology of multiple sclerosis. Annu Rev Immunol 23:683-747 (2005).

Martin, R. Immunotherapy of multiple sclerosis: where are we? where should we go?. Nature Immunology 2(9)785-8 (2001).

Murarro, PA. Molecular tracking of antigen-specific T cell clones in neurological immune-mediated disorders. Brain 126:20-31 (2003).

Pender, MP. A study of human T cell lines generated from multiple sclerosis patients and controls by stimulation with peptides of myelin basic protein. Journal of Neuroimmunology 70(1):65-74 (1996).

Lutton, JD. Multiple sclerosis: etiological mechanisms and future directions. Exp Biol Med 229:12-20 (2004).

Dornmair, K. T-cell mediated autoimmunity. Am J Pathol 163(4):1215-26 (2003).

Soderstorm, M. T cells recognizing multiple peptides of myelin basic protein are found in blood and enriched in cerebrospinal fluid in optic neuritis and multiple sclerosis. Scand J Immunol 37:355-68 (1993).

Kappos, L. Induction of a non-encephalitogenic type 2 T helper-cell autoimmune response in multiple sclerosis after administration of an altered peptide ligand in a placebo-controlled, randomized phase II trial. Nature Medicine 6(9):1176-82 (2002).

Wiendl, H. Therapeutic approaches in multiple sclerosis. Biodrugs 16(3): 183-200 (2002).

Bielekova, B. Encephalitogenic potential of the myelin basic protein peptide (amino acids 83-99) in multiple sclerosis: results of a phase II clinical trial with an altered peptide ligand. Nature Medicine 6(10): 1167-75 (2000).

Wucherpfennig, KW. Recognition of the immunodominant myelin basic protein peptide by autoantibodies and HLA-DR2-resrticted T cell clones from multiple sclerosis patients. J Clin Invest 100(5): 1114-22 (1997).

Meinl, E. Myelin basic protein-specific T lymphocyte repertoire in multiple sclerosis. J Clin Invest 92: 2633-43 (1993).

Hermans, G. et al. Cellular and humoral immune responses against autoreactive T cells in multiple sclerosis patients after T cell vaccination. Journal of Autoimmunity 13:233-46 (1999).

Hermans, G. et al. Myelin reactive T cells after T cell vaccination in multiple sclerosis: cytokine profile and depletion by additional immunizations. Journal of Neuroimmunology 102:79-84 (2000).

Stinissen, P. et al. gamma-delta T cell responses to activated T cells in multiple sclerosis patients induced by T cell vaccination. Journal of Neuroimmunology 87:94-104 (1998).

Warren, K.G. et al. Purification of primary antibodies of the myelin basic protein antibody cascade from multiple sclerosis patients: immunoreactivity studies with homologous and heterologous antigens. Clin Invest Med 15(1): 18-29 (1992).

Zhang, J. Multiple sclerosis: perspectives on autoimmune pathology and prospects for therapy. Current Neurology 15:115-55 (1995).

Zhang, J. et al. In vivo clonotypic regulation of human myelin basic protein-reactive T cells by T cell vaccination. Journal of Immunology 155:5868-77 (1995).

Zhang, J. et al. Myelin basic protein-reactive T cells in multiple sclerosis: pathologic relevance and therapeutic targeting. Cytotechnology 16:181-87 (1994).

Zhang, J. et al. T cell vaccination in multiple sclerosis: hopes and facts. 94:112-15 (1994).

Zipp, F. et al. Diversity of the anti-T-cell receptor immune response and its implications for T-cell vaccination therapy of multiple sclerosis. Brain 121:1395-1407 (1998).

Johnson et al. Copolymer 1 reduces relapse rate and improves disability in relapsing-remitting multiple sclerosis. Neurol 45:1268-76 (1995).

Zhang, J., et al. Vaccination with Myelin-Reactive T cells: Results of a Clinical Trial in Patients with Multiple Sclerosis. Neurology, 2001;54(7), Supp. 3:A23.

Zhang, J. et al. T cell vaccination in multiple sclerosis. Multiple sclerosis 1(6): 353-56 (1996).

Zang, YCQ. et al. Th2 immune regulation induced by T cell vaccination in patients with multiple sclerosis. Eur J Immunol 60(3) 908-13 (2000).

Zhang, J. et al. T-cell vaccination: clinical application in autoimmune diseases. J Mol Med 74(11): 653-62 (1996).

Stinissen, P. et al. Vaccination with autoreactive T-cell clones in multiple sclerosis: overview of immunological and clinical data. J Neurosci Res 45(4): 500-11 (1996).

Zhang, J. et al. T-cell vaccination in multiple sclerosis: Results of a preliminary study. J. Neurol. 2002:243(2):212-8.

Hafler, D. et al. T-cell vaccination in multiple sclerosis: a preliminary report. Clin Immunol Immunopathol 62(3): 307-13 (1992).

Allegretta, M. et al. T cells responsive to myelin basic protein in patients with mulitple sclerosis. Science 247:718-21 (1990).

Ben-Nun, A. et al. The rapid isolation of clonable antigen-specific T-cell lymphocyte lines capable of mediating autoimmune encephalomylitis. Eur J Immunol 11:195-204 (1981).

Ben-Nun, A. et al. Vaccination against autoimmune encephalomyelitis with T lymphocyte line cells reactive against myelin basic protein. Nature 292:60-61 (1981).

Chou, YK. et al. Frequency of T cell specific for myelin basic protein and myelin proteolipid protein in blood and cerebrospinal fluid in multiple sclerosis. J Neuroimmunol 38:105-14 (1992).

Correale et al. T cell vaccination in secondary progressive multiple sclerosis. J Neuroimmunol 107:130-39 (2000).

European Study Group on Interferon Beta 1-b in Secondary Progressive MS. Placebo-controlled mulitcentre randomized trial of interferon beta 1-b in treatment of secondary progressive multiple sclerosis. Lancet 352:1491-97 (1998).

Genain. Antibody facilitation of multiple sclerosis-like lesions in a nonhuman primate. J Clin Invest 96:2966-74 (1995).

Hafler et al. T cell vaccination in multiple sclerosis: a preliminary report. Clinical Immunol and Immunopathology 62:307-13 (1992).

Hong et al. A common T cell receptor V-D-J sequence in V∃13.1 T cells recognizing an immunodominant peptide og myelin basic protein in multiple sclerosis. J Immunol 163:3530-38 (1999).

Hong et al. Reactivity and regulatory properties of human anitidiotypic antibodies induced by t cell vaccination. J Immunol 165:6858-64 (2000).

Jacobs. Intramuscular interferon beta-1a for disease progression in relapsing multiple sclerosis. Ann Neurol 39:285-94 (1996).

Kerlero De Rosbo et al. Reactivity to myelin antigens in multiple sclerosis: peripheral blood lymphocytes respond predominantly to myelin oligodendrocyte glycoprotein. J Clin Invest 92:2602-08 (1993).

Lider. Anti-idiotypic network induced by T cell vaccination against experimental autoimmune encephalomyelitis. Science 239:181-83 (1988).

Lindert et al. Multiple sclerosis: B- and T-cell responses to the extracellular domain of the myelin oligodendrocyte glycoprotein. Brain 122:2089-99 (1999).

Lohse AW. et al. Control of experimental autoimmune encephalomyelitis by T cells responding to activated T cells. Science 244:820-22 (1989).

Markovic-Plese et al. T cell recognition of immunodominant and cryptic proteolipid protein epitopes in humans. J Immunol 155:982-92 (1995).

Medaer. Depletion of myelin basic protein-reactive T cells by T cell vaccination: a pilot clinical trial in multiple sclerosis. Lancet 346:807-808 (1995).

Naparstek et al. T lymphocyte lines producing or vaccinating against autoimmune encephalomyelitis (EAE): funtional activation induces peanut agglutinin receptors and accumulation in the brain and thymus of line cells. Eur J Immunol 13:418-23 (1983).

Ota et al. T cell recognition of an irnmunodominant MBP epitope in multiple sclerosis. Nature 346: 183-87 (1990).

Offner et al. Lymphocyte vaccination against experimental autoimmune encephalomyelitis: evaluation of vaccination protocols. J Neuroimmunol 21:13-22 (1989).

Poser et al. New disgnostic criteria for multiple sclerosis: guidelines for research protocols. Ann Neurol 13:227-31 (1983).

Scheltens et al. White matter lesions on magnetic resonance imaging in clinically diagnosed Alzheimer's disease. Brain 115:735-48 (1992).

Selmaj et al. Identification of lymphotoxin and tumor necrosis factor in multiple sclerosis lesions. J Clin Invest 87:949-54 (1991).

Sharief MK. et al. Association between tumor necrosis factor-alpha and disease progressoin in patients with multiple sclerosis. N Engl J Med 325:467-472 (1991).

Stinissen et al. Autoimmune pathogenesis of multiple sclerosis: role of autoreactive T lymphocytes and new immunotherapeutic strategies. Crit Rev Immunol 17:33-75 (1997).

The IFNB Multiple Sclerosis Study Group. Interferon beta-1b is effective in relapsing-remitting multiple sclerosis: I clinical results of a multicenter, randomized, double-blind, placebo-controlled trial. Neurol 43: 655-61 (1993).

Trotter et al. T cell recognition of myelin proteolipid protein and myelin proteolipid protein peptides in the peripheral blood of multiple sclerosis and control subjects. J Neuroimmunology 84:172-78 (1998).

Trotter et al. HPRT mutant T cell lines from multiple sclerosis patients recognize myelin proteolipid protein peptides. J Neuroimmunol 75:95-103 (1997).

Truyen et al. Improved correlation of magnetic resonance imaging (MRI) with clinical status in multiple sclerosis (MS) by use of extensive standardized imaging-protocol. J Neurol Sci 96:173-82 (1990).

Tuohy et al. Spontaneous regression of primary autoreactivity during chronic progression of experimental autoimmune encephalomyelitis and multiple sclerosis. J Exp Med 189:1033-42 (1999).

Vandevyver et al. Clonal expansion of myelin basic protein-reactive T cells in patients with multiple sclerosis: restricted T cell receptor V gene rearrangements and CDR3 sequence. Eur J Immunol 25:958-68 (1995).

Wucherpfennig et al. Clonal expansion and persistence of human T cells specific for an immunodominant myelin basic protein peptide. J Immunol 152:5581-92 (1994).

Zang et al. Immunoregulation and blocking antibodies induced by interferon beta treatment in MS. Neurobiology 55: 397-404 (2000).

Zang et al. Aberrant T cell migration toward Rantes and MIP-1alpha in patients with multiple sclerosis overexpression of chemokine receptor CCR5. Brain 123:1874-82 (2000).

Zang et al. Regulation of chemokine receptor CCR5 and production of Rantes and MIP-1alpha by interferon-beta. J Neuroimmunol 112:174-80 (2001).

Zhang and Raus. T cell vaccination in autoimmune diseases from laboratory to clinic. Human Immunol 38:87-96 (1993).

Zhang et al. Increased frequency of interleukin 2-responsive T cells specific for myelin basic protein and proteolipid protein in peripheral blood and cerebrospinal fluid of patients with multiple sclerosis. J Exp Med 179:973-84 (1994).

Zhang et al. In vivo clonotypic regualtion of human myelin basic protein-reactive T cells by T cell vaccination. J Immunol 155:5868-77 (1995).

Zhang, J. et al. Myelin basic protein-specific T lymphocytes in multiple sclerosis and controls: precursor frequency, fine specificity, and cytotoxicity. Ann of Neurology 32(3): 330-38 (1992).

Correale, J et al. Isolation and characterization of autoreactive proteolipid protein specific T-cell clones from multiple sclerosis patients. Neurology, 1995;45:1370-8.

Warren, KG et al. Anti-myelin basic protein and anti-proteolipid protein specific forms of multiple sclerosis. Ann Neurol, 1994;35:280-9.

Olsson, T et al. Autoreactive T lymphocytes in multiple sclerosis determined by antigen-induced secretion of interferon-gamma. J Clin Invest, 1990;86:981-5.

Zhang, J et al. T-cell vaccination in autoimmune diseases. Human Immunology, 1993;38:87-96.

Achiron, A. T-cell vaccination in multiple sclerosis. Autoimmunity Reviews, 2004;3:25-32.

Achiron, A et al. T cell vaccination in multiple sclerosis relapsing-remitting nonresponders patients. Clinical Immunology, 2004;113:155-160.

Ben-Nun, A. The autoimmune reactivity to myelin oligodendrocyte glycoprotein (MOG) in multiple sclerosis is potentially pathogenic: effect of copolymer 1 on MOG-induced diseases. Journal Neurol, 1996;243(1):S14-S22.

Ben-Nun, A. The rapid isolation of clonable antigen-specific T lymphocyte lines capable of mediating autoimmune encephalomyelitis. Eur Journal Immunol, 1981;11:195-9.

Ben-Nun, A. Vaccination against autoimmune encephalomyelitis with T lymphocyte line cells reactive against myelin basic protein. Nature, 1981;292(5919):60-1.

Hellings, N et al. T cell vaccination in multiple sclerosis: update on clinical application and mode of action. Autoimmunity Reviews, 2004;3:267-75.

* cited by examiner

```
SEQUENCE LISTING

<160> NUMBER OF SEQ ID NOS: 6

<210> SEQ ID NO 1
<211> LENGTH: 17
<212> TYPE: PRT
<213> ORGANISM: Artificial
<220> FEATURE:
<221> NAME/KEY: PEPTIDE
<222> LOCATION: (1)..(17)
<223> OTHER INFORMATION: amino acids 110 to 126 of human myelin basic
      protein

<400> SEQUENCE: 1

Glu Asn Pro Val Val His Phe Phe Lys Asn Ile Val Thr Pro Arg Thr
1               5                   10                  15

Pro

<210> SEQ ID NO 2
<211> LENGTH: 20
<212> TYPE: PRT
<213> ORGANISM: Artificial
<220> FEATURE:
<221> NAME/KEY: PEPTIDE
<222> LOCATION: (1)..(20)
<223> OTHER INFORMATION: amino acids 167 to 186 of human mylelin basic
      protein

<400> SEQUENCE: 2

Ser Lys Ile Phe Lys Leu Gly Gly Arg Asp Ser Arg Ser Gly Ser Pro
1               5                   10                  15

Met Ala Arg Arg
            20

<210> SEQ ID NO 3
<211> LENGTH: 20
```

```
<212> TYPE: PRT
<213> ORGANISM: Artificial
<220> FEATURE:
<221> NAME/KEY: PEPTIDE
<222> LOCATION: (1)..(20)
<223> OTHER INFORMATION: amino acids 31 to 50 of human myelin
      proteolipid protein

<400> SEQUENCE: 3

Leu Phe Cys Gly Cys Gly His Glu Ala Leu Thr Gly Thr Glu Lys Leu
1               5                   10                  15

Ile Glu Thr Tyr
            20

<210> SEQ ID NO 4
<211> LENGTH: 20
<212> TYPE: PRT
<213> ORGANISM: Artificial
<220> FEATURE:
<221> NAME/KEY: PEPTIDE
<222> LOCATION: (1)..(20)
<223> OTHER INFORMATION: amino acids 181 to 200 of human myelin
      proteolipid protein

<400> SEQUENCE: 4

Trp Thr Thr Cys Gln Ser Ile Ala Phe Pro Ser Lys Thr Ser Ala Ser
1               5                   10                  15

Ile Gly Ser Leu
            20

<210> SEQ ID NO 5
<211> LENGTH: 17
<212> TYPE: PRT
<213> ORGANISM: Artificial
<220> FEATURE:
<221> NAME/KEY: PEPTIDE
<222> LOCATION: (1)..(17)
<223> OTHER INFORMATION: amino acids 1 to 17 of human myelin
      oligodendrocyte glycoprotein

<400> SEQUENCE: 5

Gly Gln Phe Arg Val Ile Gly Pro Arg His Pro Ile Arg Ala Leu Val
1               5                   10                  15

Gly

<210> SEQ ID NO 6
<211> LENGTH: 21
<212> TYPE: PRT
<213> ORGANISM: Artificial
<220> FEATURE:
<221> NAME/KEY: PEPTIDE
<222> LOCATION: (1)..(21)
<223> OTHER INFORMATION: amino acids 18 to 38 of human myelin
      oligodendrocyte glycoprotein

<400> SEQUENCE: 6

Glu Val Glu Leu Pro Cys Arg Ile Ser Pro Gly Lys Asn Ala Thr Gly
1               5                   10                  15

Met Glu Val Gly Trp
            20
```

ISOLATION AND IDENTIFICATION OF T CELLS

CROSS REFERENCE TO RELATED APPLICATIONS

This application is the National Stage of International Application Number PCT/US2003/024548, filed Aug. 6, 2003, which claims the benefit of U.S. Provisional Application No. 60/402,521, filed Aug. 8, 2002.

FIELD OF THE INVENTION

The present invention relates generally to the field of diagnosis and treatment of autoimmune disease, such as multiple sclerosis (MS). More particularly, it concerns the isolation of antigen-specific T cells. In addition, the present invention concerns the use of antigen-specific T cells for the treatment of autoimmune disease, such as MS.

BACKGROUND

Intercellular recognition complexes formed by T cell receptors (TCR) on cytotoxic T lymphocytes or T helper cells and MHC/peptide complexes on antigen presenting cells (APC) are a common recognition component in a diverse set of cell-cell encounters that activate T cells both during the development of the repertoire of T cells within an individual organism (positive selection; negative selection; peripheral survival) and during the control (T helper) and effector stages (T killer) of an adaptive immune response.

In the adaptive immune response, antigens are recognized by hypervariable molecules, such as antibodies or TCRs, which are expressed with sufficiently diverse structures to be able to recognize any antigen. Antibodies can bind to any part of the surface of an antigen. TCRs, however, are restricted to binding to short peptides bound to class I or class II molecules of the major histocompatibility complex (MHC) on the surface of APCs. TCR recognition of a peptide/MHC complex triggers activation (clonal expansion) of the T cell.

TCRs are heterodimers composed of two chains which can be $\alpha\beta$ (alpha-beta) or $\gamma\delta$ (gamma-delta). The structure of TCRs is very similar to that of immunoglobulins (Ig). Each chain has two extracellular domains, which are immunoglobulin folds. The amino-terminal domain is highly variable and called the variable (V) domain. The domain closest to the membrane is the constant (C) domain. These two domains are analogous to those of immunoglobulins, and resemble Fab fragments. The V domain of each chain has three complementarity determining regions (CDR). Proximal to the membrane, each TCR chain has a short connecting sequence with a cysteine residue that forms a disulfide bond between both chains.

Genes encoding $\alpha\beta$ and $\gamma\delta$ heterodimers are only expressed in the T-cell lineage. The four TCR loci ($\alpha$, $\beta$, $\gamma$ and $\delta$) have a germ-line organization very similar to that of Ig. $\alpha$ and $\gamma$ chains are produced by rearrangements of V and J segments whereas $\beta$ and $\delta$ chains are produced by rearrangements of V, D, and J segments. The gene segments for TCR chains are located on different chromosomes, except the $\delta$-chain gene segments that are between the V and J gene segments of the $\alpha$ chain. The location of $\delta$-chain gene segments has a significance: a productive rearrangement of $\alpha$-chain gene segments deletes C genes of the $\delta$-chain, so that in a given cell the $\alpha\beta$ heterodimer cannot be co-expressed with the $\gamma\delta$ receptor.

In mice, there are about 100 V$\alpha$ and 50 J$\alpha$ genes segments and only one C$\alpha$ segment. The $\delta$-chain gene family has about 10 V, 2 D, and 2 J gene segments. The $\beta$-chain gene family has 20-30 V segments and two identical repeats containing 1 D$\beta$, 6 J$\beta$ and 1 C$\beta$. Finally, the $\gamma$-chain gene family contains 7 V and 3 different J-C repeats. In humans the organization is similar to that of mice, but the number of segments varies.

The rearrangements of gene segments in $\alpha$ and $\beta$ chains is similar to that of Igs. The $\alpha$ chain, like the light chain of Ig is encoded by V, J, and C gene segments. The $\beta$ chain, like the heavy chain of Ig, is encoded by V, D, and J gene segments. Rearrangements of $\alpha$ chain gene segments result in VJ joining and rearrangements of $\beta$ chain result in VDJ joining. After transcription of rearranged genes, RNA processing, and translation, the $\alpha$ and $\beta$ chains are expressed linked by a disulfide bond in the membrane of T cells.

TCR gene segments are flanked by recognition signal sequences (RSS) containing a heptamer and a nonamer with an intervening sequence of either 12 nucleotides (one turn) or 23 nucleotides (two turn). As in Igs, enzymes encoded by recombination-activating genes (RAG-1 and RAG-2) are responsible for the recombination processes. RAG1/2 recognize the RSS and join V-J and V-D-J segments in the same manner as in Ig rearrangements. Briefly, these enzymes cut one DNA strand between the gene segment and the RSS and catalyze the formation of a hairpin in the coding sequence. The signal sequence is subsequently excised.

The combinatorial joining of V and I segments in $\alpha$ chains and V, D and J segments in $\beta$ chains produces a large number of possible molecules, thereby creating a diversity of TCRs. Diversity is also achieved in TCRs by alternative joining of gene segments. In contrast to Ig, $\beta$ and $\delta$ gene segments can be joined in alternative ways. RSS flanking gene segments in $\beta$ and $\delta$ gene segments can generate VJ and VDJ in the $\beta$ chain, and VJ, VDJ, and VDDJ on the $\delta$ chain. As in the case of Ig, diversity is also produced by variability in the joining of gene segments.

Hypervariable loops of the TCR known as complementarity determining regions (CDRs) recognize the composite surface made from a MHC molecule and a bound peptide. The CDR2 loops of $\alpha$ and $\beta$ contact only the MHC molecule on the surface of APC, while the CDR1 and CDR3 loops contact both the peptide and MHC molecule. Compared with Ig, TCRs have more limited diversity in the CDR1 and CDR2. However, diversity of the CDR3 loops in TCRs is higher than that of Ig, because TCRs can join more than one D segment leading to augmented junctional diversity.

The pathogenesis of a number of autoimmune diseases is believed to be caused by autoimmune T cell responses to self-antigens present in the organism. Not all autoreactive T cells are deleted in the thymus, in contradiction with the clonal selection paradigm. Those T cells with TCRs for a broad spectrum of self-antigens represent part of the normal T-cell repertoire and naturally circulate in the periphery. It is unclear why autoreactive T cells are allowed, during their evolution, to undergo differentiation in the thymus and are accommodated in the periphery. While their physiological role is not understood, these autoreactive T cells, when activated, present a potential risk in the induction of autoimmune pathologies. Autoreactive T cells can also be isolated from normal individuals without the consequences of autoimmune diseases. It has been established that antigen recognition of autoreactivity by itself is not sufficient to mediate the autodestructive process. One of the prerequisites for autoreactive T cells to be pathogenic is that they must be activated.

Autoreactive T cells are implicated in the pathogenesis of autoimmune diseases, such as multiple sclerosis (MS) and rheumatoid arthritis (RA). The pathogenesis of autoreactive T cells in MS is generally held to arise from T cell responses to myelin antigens, in particular myelin basic protein (MBP). MBP-reactive T cells are found to undergo in vivo activation, and occur at a higher precursor frequency in blood and cerebrospinal fluid in patients with MS as opposed to control individuals. These MBP-reactive T cells produce $T_H1$ cytokines, e.g. IL-2, TNFα, and γ-interferon (IFNγ), which facilitate migration of inflammatory cells into the central nervous system and exacerbate myelin-destructive inflammatory responses in MS.

Myelin-reactive T cells have also been shown to be involved in the pathogenesis of experimental autoimmune encephalomyelitis (EAE) in animals, which resembles MS. EAE can be induced actively in susceptible animals by injecting myelin proteins emulsified in an adjuvant or passively by injecting myelin-reactive T-cell lines and clones derived from myelin-sensitized animals. When activated in vitro, very small numbers of myelin-reactive T cells are required to induce EAE, while 100-fold more resting T cells with the same reactivity are incapable of mediating EAE.

EAE has been shown to be prevented and also treated by vaccination with inactivated myelin-reactive T cells, a procedure called T-cell vaccination (Ben-Nun et al., Nature, 1981; 292: 60-61). T-cell vaccination induces regulatory immune responses comprised of anti-idiotypic T cells and anti-ergotypic T cells, which lead to the depletion of myelin-reactive T cells. By depleting myelin-reactive T cells, therapeutic effects are observed in EAE and other experimental autoimmune disease models (Lider et al., Science, 1988; 239:820-822; Lohse et al., Science, 1989; 244: 820-822).

Due to the success in autoimmune disease models, T cell vaccination has recently advanced to clinical trials in patients with MS. Based on the results in experimental models such as EAE, it is believed that depletion of autoreactive T cells may improve the clinical course of MS and other autoimmune diseases.

In a pilot clinical trial, vaccination with irradiated autologous MBP-reactive T cell clones elicited CD8+ cytolytic T cell responses that specifically recognized and lysed circulating MBP-reactive T cells (Zhang et al., Science, 1993; 261: 1451-1454, Medaer et al., Lancet 1995: 346:807-808). Three subcutaneous inoculations with irradiated MBP-reactive T cell clones resulted in the depletion of circulating MBP-reactive T cells in patients with MS.

In a preliminary clinical trial, circulating MBP-reactive T cells were depleted in relapsing remitting MS patients and secondary progressive MS patients (Zhang et al., J Neurol., 2002; 249:212-8), by vaccinating the patients with three subcutaneous injections of irradiated autologous MBP-reactive T cells. T cell vaccination was beneficial to each group of patients as measured by rate of relapse, expanded disability scale score and MRI lesion activity. However, there was a trend for an accelerated progression after about twelve months following the last injection. The significance of the apparent accelerated progression is unknown, but may be associated with a gradual decline of the immunity induced by T cell vaccination against MBP-reactive T cells. In approximately 10-12% of the immunized patients, MBP-reactive T cells reappeared at about the same time as the accelerated progression. In some cases, the reappearing MBP-reactive T cells originated from different clonal populations that were not detected before vaccination, suggesting that MBP-reactive T cells may undergo clonal shift or epitope spreading. Clonal shift of MBP-reactive T cells has been observed in previous studies (Zhang et al. 1995) and may be associated with the on-going disease process.

Although T cell vaccination has been demonstrated to be effective for depleting myelin-reactive T cells and potentially beneficial for MS patients, there are several problems with the treatment. T cell vaccine treatment for each patient must be individualized because the T cell receptors of myelin-reactive T cells are highly diverse and vary between different MS patients (Vandevyver et al., Eur. J. Immunol., 1995; 25:958-968, Wucherpfennig et al., J. Immunol., 1994; 152:5581-5592, Hong et al., J. Immunol., 1999; 163:3530-3538).

In addition to being individualized for each patient, up to 8 weeks is required to produce a given T cell vaccine using current procedures. Production of a T cell vaccine begins with isolating mononuclear cells from the cerebrospinal fluid (CS-FMCs) or peripheral blood (PBMCs) of a patient. The isolated mononuclear cells are then cultured with myelin peptides for 7-10 days to activate myelin-reactive T cells. Cultures are then tested for specific proliferation to myelin peptides by measuring [$^3$H]-thymidine incorporation in the presence of myelin peptides over a period of 3 days. Cultures testing positive for specific proliferation to myelin peptides are then serially diluted to obtain clonal T cell lines or directly expanded. The cells are then cultured up to 6-8 weeks to expand the T cells. When the final T cell vaccine product is clonal, the T cells are homogenous with a single pattern of Vβ-Dβ-Jβ gene usage. Usually, three to six of the clonal cell lines are combined to produce a heterogeneous formulation with multiple patterns of Vβ-Dβ-Jβ gene usage. When the final T cell vaccine product is produced by direct expansion, the T cells are heterogeneous with more than one pattern of Vβ-Dβ-Jβ gene usage.

The individualized nature of T cell vaccination and the prolonged cell culture needed for production of each vaccine make treatment expensive and labor intensive under current methodologies. The extended time required for cell culture also creates a significant risk of contamination. Finally, the likelihood of clonal shift or epitope spreading of myelin-reactive T cells may require the subsequent production of a T cell vaccine for each patient with a different pattern of Vβ-Dβ-Jβ gene usage.

Therefore, there exists a need to develop improved methods of isolating T cells with specificity for antigens, such as MBP, that may be used to produce T cell vaccines for the treatment of patients with T cell-mediated diseases such as MS. There also exists a need to develop improved methods for producing T cell vaccines with a heterogeneous pattern of Vβ-Dβ-Jβ gene usage to account for clonal shift of autoreactive T cells.

SUMMARY OF THE INVENTION

The present invention is generally directed to methods of isolating antigen-specific T cells and more particularly T cells specific for self or autoantigens. The methods for isolating one or more T cells specific for an antigen of interest generally comprise incubating a sample comprising T cells obtained from a patient with said antigen or a derivative thereof; selecting one or more T cells that express one or more first markers selected from the group consisting of CD69, CD4, CD25, CD36 and HLADR; and one or more second markers selected from the group consisting of IL-2, IFNg, TNFα, IL5, IL-10 and IL-13.

The methods of the invention are particularly useful for isolating autoreactive T cells which play a role in the pathogenesis of autoimmune diseases.

The methods of the invention also permit the diagnosis of autoimmune disease as well as monitoring the progression of the disease and for monitoring the efficacy of treatments for the disease.

The methods of the invention also allow the preparation of autologous T cell vaccines for the treatment of T cell related autoimmune diseases.

The methods for vaccine preparation generally involve the isolation of antigen-specific T cells as described above optionally followed by subsequent culturing steps which allows the expansion of the population of isolated antigen-specific T cells.

The invention inter alia is also directed to T cell vaccines and pharmaceutical compositions comprising antigen-specific T cells isolated using the methods of the invention.

The methods of the invention are also useful for characterizing T cell receptors and their encoding nucleic acids.

DETAILED DESCRIPTION

1. Definitions

Figure 1:
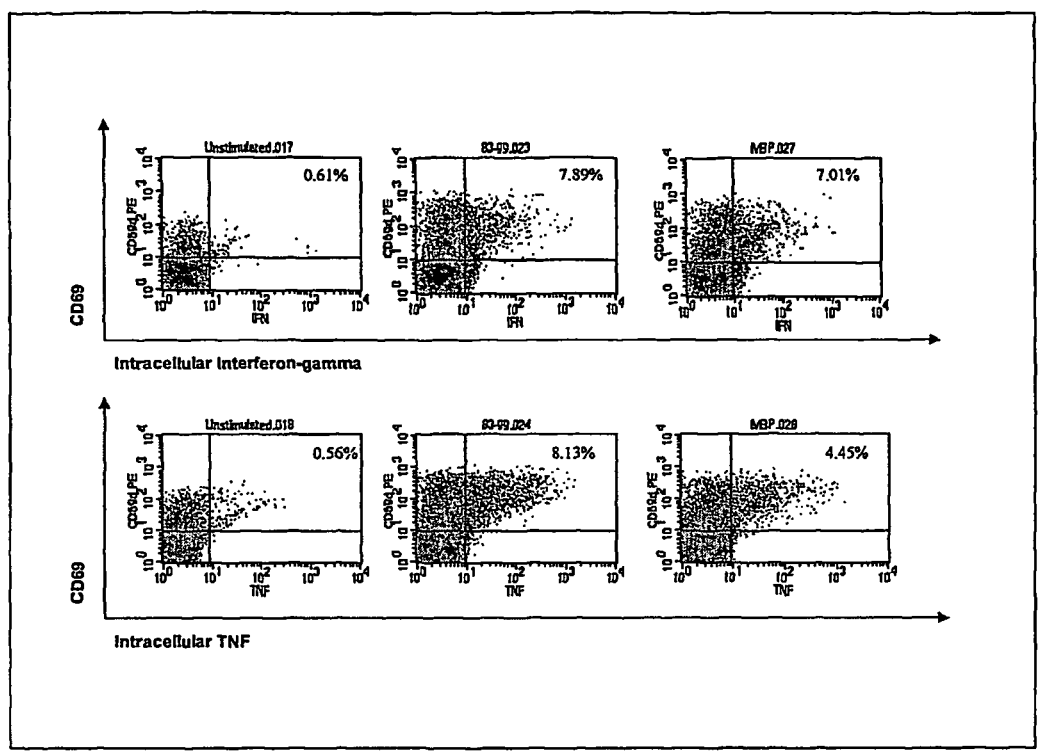
FIG. 1 demonstrates FACS identification of cells expressing CD69 and γIFN (top) and CD69 and TNFα (bottom) in a multiple sclerosis patient before stimulation (left), after stimulation with residues 83-99 of MBP (middle), and after stimulation with residues 83-99 of MBP (right).

To aid in the understanding of the present invention, several terms are defined below.

"Autoantigen" or "self-antigen" as used herein refers to an antigen or epitope which is native to the mammal which is immunogenic in said mammal disease is conserved in that species of mammal and which may be involved in the pathogenesis of autoimmune.

"CD," "cluster of differentiation" or "common determinant" as used herein refers to cell surface molecules recognized by antibodies. Expression of some CDs is specific for cells of a particular lineage or maturational pathway, and the expression of others varies according to the state of activation, position, or differentiation of the same cells.

"Derived from" or "a derivative thereof," in the context of nucleotide sequences means that the nucleotide sequence is not limited to the specific sequence described, but also includes variations in that sequence, which may include nucleotide additions, deletions, substitutions, or modifications to the extent that the variations to the described sequence retain the ability to hybridize under moderate or highly stringent conditions to the complement of the described sequence. In the context of peptide or polypeptide sequences, "derived from" or "a derivative thereof" means that the peptide or polypeptide is not limited to the specific sequence described, but also includes variations in that sequence, which may include amino acid additions, deletions, substitutions, or modifications to the extent that the variations in the listed sequence retain the ability to elicit an immune response to the described sequence.

"Immunogenic," when used to describe a peptide or polypeptide, means the peptide or polypeptide is able to induce an immune response, either T cell mediated, antibody, or both.

"Immune-related disease" means a disease in which the immune system is involved in the pathogenesis of the disease. A subset of immune-related diseases are autoimmune diseases. Autoimmune diseases include, but are not limited to, rheumatoid arthritis, myasthenia gravis, multiple sclerosis, psoriasis, systemic lupus erythematosus, autoimmune thyroiditis (Hashimoto's thyroiditis), Graves' disease, inflammatory bowel disease, autoimmune uveoretinitis, polymyositis, and certain types of diabetes. In view of the present disclosure, one skilled in the art can readily perceive other autoimmune diseases treatable by the compositions and methods of the present invention.

"PCR" means the polymerase chain reaction, for example, as generally described in U.S. Pat. No. 4,683,202 (issued Jul. 28, 1987 to Mullis), which is incorporated herein by reference. PCR is an amplification technique wherein selected oligonucleotides, or primers, may be hybridized to nucleic acid templates in the presence of a polymerization agent (such as a DNA or RNA polymerase) and nucleotide triphosphates, whereby extension products may be formed from the primers. These products may then be denatured and used as templates in a cycling reaction that amplifies the number and amount of existing nucleic acids which may facilitate their subsequent detection. A variety of PCR techniques are known in the art and may be used in connection with the disclosure herein.

A "Peptide" or "polypeptide" is a linked sequence of amino acids and may be natural, synthetic, or a modification or combination of natural and synthetic.

"Primer" means an oligonucleotide, whether natural, synthetic, or a modification thereof, capable of acting as a point of initiation of nucleotide synthesis sufficiently complementary to a specific nucleotide sequence on a template molecule.

"Probe" means an oligonucleotide, whether natural, synthetic, or a modification thereof, capable of specifically binding to a sufficiently complementary nucleotide sequence.

"T cell mediated disease" means a disease arising as a result of T cells recognizing self-antigens.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Isolation of Antigen-Specific T Cells a. Isolation of Monoclonal Antigen-Specific T Cells T cells may be activated and expanded in cell culture by incubation with an antigen target and antigen presenting cells. Once activated, T cells undergo a complex cascade of cell signaling which leads to the transcription and expression of many gene products. The invention described herein takes advantage of gene products specific for activated T cells for the identification and isolation of T cells with desired antigen specificity.

In a first aspect, the present invention is directed to a method for isolating a T cell that is specific for an antigen of interest. A sample comprising T cells is incubated with a particular antigen, which causes the activation of a T cell specific for the antigen of interest. The sample may be incubated with the antigen for 1 to 7 days. The sample may also be incubated with the antigen for less than 1 day. The sample may also be incubated with the antigen for less than 16 hours.

The sample may also be incubated with the antigen for less than 12 hours. The sample may also be incubated with the antigen for less than 8 hours. The sample may also be incubated with the antigen for less than 4 hours. The sample may also be incubated with the antigen for less than 2 hours.

A T cell specific for the antigen of interest may then be isolated by selecting for T cells that express gene products of T cells activated as described above. Subsets of activated T cells may be isolated by selecting for T cells with subset-specific gene products or cell surface markers (e.g., CD4 vs. CD8).

The antigen of interest includes myelin basic protein (MBP), proteolipid protein (PLP), myelin oligodendrocyte glycoprotein (MOG), or a fragment thereof. The antigen of interest may also be an immunodominant fragment including, but not limited to, residues 83-99 or residue 151-170 of MBP. The antigen of interest may also be a combination of two or more individual antigens of interest.

The antigen or a derivative thereof, used to activate the T cells may be any immunogen which is capable of eliciting an immune response to the antigen of interest. The activating antigen may be the antigen of interest, or a derivative thereof. The activating antigen may be MBP, PLP, MOG, or a fragment and/or derivative thereof. The activating antigen may also be an immunodominant fragment including, but not limited to, residues 83-99 or residue 151-170 of MBP, or a fragment and/or derivative thereof. The activating antigen may also be a combination of two or more individual activating antigens. The activating antigen may be used one or more times to activate T cells specific for an antigen of interest The T cells may be present in any sample comprising mononuclear cells. The sample may be isolated from the peripheral blood or cerebral spinal fluid of an MS patient or from the synovial fluid of a RA patient. T cells from patients with other autoimmune diseases may be similarly isolated from peripheral blood and/or tissues involved with the disease. Mononuclear cells may be enriched in the sample by using centrifugation techniques known to those in the art including, but not limited to, Ficoll® gradients. T cells may also be enriched in the sample by using positive selection, negative selection, or a combination thereof for expression of gene products of T cells.

The gene product for identifying or negatively selecting for activated T cells may be a cell surface marker or cytokine, or a combination thereof. Cell surface markers for identifying activated T cells include, but are not limited to, CD69, CD4, CD8, CD25, HLA-DR, CD28, and CD134. CD69 is an early activation marker found on B and T lymphocytes, NK cells and granulocytes. CD25 is an IL-2 receptor and is a marker for activated T cells and B cells. CD4 is a TCR coreceptor and is marker for thymoctes, $T_H1$- and $T_H2$-type T cells, monocytes, and macrophages. CD8 is also a TCR coreceptor and is marker for cytotoxic T cells. CD134 is expressed only in activated CD4$^+$ T cells.

Cell surface markers for negatively selecting for activated T cells include, but are not limited to, CD36, CD40, and CD44. CD28 acts as a stimulatory T-cell activation pathway independent of the T-cell receptor pathway and is expressed on CD4$^+$ and CD8$^+$ cells. CD36 is a membrane glycoprotein and is a marker for platelets, monocytes and endothelial cells. CD40 is a marker for B cells, macrophages and dendritic cells. CD44 is a marker for macrophages and other phagocytic cells. Subsets of T cells may be isolated by using positive selection, negative selection, or a combination thereof for expression of cell surface gene products of helper T cells or cytotoxic T cells (e.g., CD4 vs. CD8).

Cytokines for identifying activated T cells of the present invention include, but are not limited to cytokines produced by $T_H1$-type T cells (cell-mediated response) and $T_H2$-type T cells (antibody response). Cytokines for identifying activated $T_H1$-type T cells include, but are not limited to, IL-2, gamma interferon (γIFN) and tissue necrosis factor alpha (TNFα). Cytokines for identifying activated $T_H2$-type T cells include, but not limited to, IL-4, IL-5, IL-10 and IL-13. Subsets of T cells may also be isolated by using positive selection, negative selection, or a combination thereof for expression of cytokine gene products of helper T cells or cytotoxic T cells (e.g., γIFN vs. IL4).

An activated $T_H1$-type T cell specific for an antigen of interest may be isolated by identifying cells that express CD69, CD4, CD25, IL-2, IFNγ, TNFα, or a combination thereof. An activated $T_H1$-type T cell specific for an antigen of interest may also be isolated by identifying cells that express CD69 and CD4 together with IFNγ or TNFα. An activated $T_H2$-type T cell specific for an antigen of interest may be isolated by identifying cells that express CD69, CD4, IL-4, IL-5, IL-10, IL-13, or a combination thereof. A combination of an activated $T_H1$-type T cell and a $T_H2$-type T cell specific for an antigen of interest may be isolated by identifying cells that express CD69, CD4, CD25, IL-2, IFNγ, TNFα, or a combination thereof and cells that express CD69, CD4, IL-4, IL-5, IL-10, IL-13, or a combination thereof/

The gene products used for positive or negative selection of the activated T cells of the present invention may be identified by immunoselection techniques known to those in the art which utilize antibodies including, but not limited to, fluorescence activated cell sorting (FACS), magnetic cell sorting, panning, and chromatography. Immunoselection of two or more markers on activated T cells may be performed in one or more steps, wherein each step positively or negatively selects for one or more markers. When immunoselection of two or more markers is performed in one step using FACS, the two or more different antibodies may be labeled with different fluorophores.

Magnetic cell sorting may be performed using super-paramagnetic microbeads composed of iron oxide and a polysaccharide coat. Preferably the microbeads may be approximately 50 nanometers in diameter, and have a volume about one-millionth that of a typical mammalian cell. The microbeads are preferably small enough to remain in colloidal suspension, which permits rapid, efficient binding to cell surface antigens. The microbeads preferably do not interfere with flow cytometry, are biodegradable, and have negligible effects on cellular functions. The antibody coupling to the microbeads may be direct or indirect, via a second antibody to a ligand such as fluorescein.

The antibody may be of classes IgG, IgM, IgA, IgD, and IgE, or fragments or derivatives thereof, including Fab, F(ab')$_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to an epitope of a gene product specific for activated T cells, or a sequence derived therefrom. The antibody may also be a chimeric antibody.

The antibody may be derivatized by the attachment of one or more chemical, peptide, or polypeptide moieties known in the art that allow the identification and/or selection of the activated T cell to which the antibody is bound. The antibody may be conjugated with a chemical moiety such as a fluorescent dye. An activated T cell bound by a fluorescently labeled antibody may be isolated using techniques including, but not limited to, fluorescence activated cell sorting (FACS). The antibody may also be conjugated with a magnetic particle, such as a paramagnetic microbead (Miltenyi Biotec, Germany). An activated T cell bound by a magnetically labeled antibody may be isolated using techniques including, but not limited to, magnetic cell sorting.

For cell-surface expressed gene products, the antibody may directly bind to the gene product and may be used for cell selection. For cell-surface gene products expressed at low concentrations, magnetofluorescent liposomes (Scheffold, et al. *Nature Med* 6:107-110, 2000) may be used for cell selection. At low levels of expression, conventional fluorescently labeled antibodies may not be sensitive enough to detect the presence of the cell surface expressed gene product. Fluorophore-containing liposomes may be conjugated to antibodies with the specificity of interest, thereby allowing detection of the cell surface expressed gene product.

For intracellular gene products, such as cytokines, the antibody may be used after permeabilizing the cells. Alternatively, to avoid killing the cells by permeabilization, the intracellular gene product if it is ultimately secreted from the cell may be detected as it is secreted through the cell membrane using a "catch" antibody on the cell surface. The catch antibody may be a double antibody that is specific for two different antigens: (i) the secreted gene product of interest and (ii) a cell surface protein. The cell surface protein may be any surface marker present on T cells, in particular, or lymphocytes, in general, (e.g., CD45). The catch antibody may first bind to the cell surface protein and then bind to the intracellular gene product of interest as it is secreted through the membrane, thereby retaining the gene product on the cell surface. A labeled antibody specific for the captured gene product may then be used to bind to the captured gene product, which allows the selection of the activated T cell (Manz, et al. *Proc. Natl. Acad. Sci. USA* 92:1921-1925, 1995, incorporated herein by reference).

Certain forms of cytokines are also found expressed at low concentration on the cell surface. For example, γIFN is displayed at a low concentration on the cell surface with kinetics similar to those of intracellular γIFN expression (Assenmacher, et al. *Eur J. Immunol,* 1996, 26:263-267). For forms of cytokines expressed on the cell surface, conventional fluorescently labeled antibodies or fluorophore containing liposomes may be used for detecting the cytokine of interest. One of ordinary skill in the art will recognize other techniques for detecting and selecting extracellular and intracellular gene products specific for activated T cells.

The T cells isolated by the present invention may be enriched by at least 90% from whole blood. The T cells may also be enriched by at least 95% from whole blood. The T cells may also be enriched by at least 98% from whole blood. The T cells may also be isolated at least 99.5% from whole blood.

b. Isolated Monoclonal Antigen-Specific T Cells

In a second aspect, the present invention is directed to a T cell specific for an antigen of interest isolated by the method of the first aspect of the present invention.

c. Isolation of Polyclonal Antigen-Specific T Cells

In a third aspect, the present invention is directed to a method for isolating T cells that are specific for one or more antigens of interest. A sample comprising T cells is incubated with one or more antigens, which cause the activation of T cells specific for one or more antigens. T cells specific for one or more antigens may then be isolated as in the first aspect of the present invention.

The T cells may have a heterogeneous pattern of Vβ-Dβ-Jβ gene usage that express different TCRs which are each specific for an antigen of interest. The T cells may also have a heterogeneous pattern of Vβ-Dβ-Jβ gene usage that express different TCRs which are specific for more than one antigen of interest. As described below, T cells comprising a heterogeneous pattern of Vβ-Dβ-Jβ gene usage may be used to formulate a polyclonal T cell vaccine which may prevent epitope spreading in vaccinated patients.

d. Isolated Polyclonal Antigen-Specific T Cells

In a fourth aspect, the present invention is directed to T cells specific for one or more antigens of interest isolated by the method of the third aspect of the present invention.

3. Quantifying the Number of Antigen-Specific T Cells

In a fifth aspect, the present invention is directed to a method of determining the relative frequency of T cells specific for one or more antigens of interest in a sample by determining the number of T cells isolated by the method of the first or third aspects of the present invention.

4. Diagnosing an Autoimmune Disease

In a sixth aspect of the present invention, a patient with an autoimmune disease may be diagnosed by obtaining a sample from a patient and isolating autoreactive T cells by the method of the first or third aspects of the present invention. The autoimmune disease may be diagnosed by comparing the level of autoreactive T cells in a patient to a control. The level of autoreactive T cells may be determined in accordance with the method of the fifth aspect of the present invention.

5. Monitoring the Progress of an Autoimmune Disease

In a seventh aspect of the present invention, an autoimmune disease may be monitored by determining the frequency of autoreactive T cells in a sample from a patient with an autoimmune disease in accordance with the fifth aspect of the present invention. The severity of symptoms of the autoimmune disease may correlate with the number of autoreactive T cells. In addition, an increase in the number of autoreactive T cells in the sample may be used as an indication to apply treatments intended to minimize the severity of the symptoms and/or treat the disease before the symptoms appear.

6. Producing a Vaccine for the Treatment of an Autoimmune Disease

In an eighth aspect of the present invention, a composition may be produced for treating an autoimmune disease by inactivating autoreactive T cells which have been isolated (and optionally expanded in culture as described herein) by the method of the first or third aspects of the present invention. The autoreactive T cells may be inactivated using a number of techniques known to those in the art including, but not limited to, chemical inactivation or irradiation. The autoreactive T cells may be preserved either before or after inactivation using a number of techniques known to those in the art including, but not limited to, cryopreservation. As described below, the composition may be used as a vaccine to deplete autoreactive T cells in autoimmune patients.

The composition may be a pharmaceutical composition, which may be produced using methods well known in the art. Pharmaceutical compositions used as preclinical and clinical therapeutics in the treatment of disease or disorders may be produced by those of skill, employing accepted principles of diagnosis and treatment. Such principles are known in the art, and are set forth, for example, in Braunwald et al., eds., Harrison's Principles of Internal Medicine, 11th Ed., McGraw-Hill, publisher, New York, N.Y. (1987), which is incorporated by reference herein. The pharmaceutical composition may be administered to any animal which may experience the beneficial effects of the composition. Animals receiving the pharmaceutical composition may be humans or other mammals.

a. Vaccine

In a ninth aspect, the present invention is drawn to a composition produced by the method of the eighth aspect of the present invention. The composition may be a vaccine, which may be used to deplete autoreactive T cells in autoimmune patients.

7. Treatment of an Autoimmune Disease

In a tenth aspect, an autoimmune disease may be treated in patients with autoreactive T cells by administering a composition according to the ninth aspect of the present invention. The composition may be a vaccine, which may lead to the depletion of autoreactive T cells in the patient.

A vaccine may comprise autoreactive T cells comprising homogeneous ("monoclonal") or heterogeneous ("polyclonal") patterns of Vβ-Dβ-Jβ gene usage. Clinical studies indicate that autoimmune patients receiving autologous monoclonal T cell vaccination may show a gradual decline in the immunity against myelin-reactive T cells. In some cases, the reappearing autoreactive T cells may originate from different clonal populations, suggesting that myelin-reactive T cells may undergo clonal shift or epitope spreading potentially associated with the ongoing disease process. Clonal shift or epitope spreading may be a problem in autoimmune diseases mediated by autoreactive T cells. A vaccine comprising polyclonal autoreactive T cells capable of depleting multiple populations of autoreactive T cells may avoid problems with clonal shift or epitope spreading.

The composition may be a pharmaceutical composition, which is administered by any means that achieve their intended purpose. For example, administration may be by parenteral, subcutaneous, intravenous, intraarterial, intradermal, intramuscular, intraperitoneal, transdermal, transmucosal, intracerebral, intrathecal, or intraventricular routes. Alternatively, or concurrently, administration may be by the oral route. The pharmaceutical compositions may be administered parenterally by bolus injection or by gradual perfusion over time.

The dosage administered may be dependent upon the age, sex, health, and weight of the recipient, kind of concurrent treatment, if any, frequency of treatment, and the nature of the effect desired. The dose ranges for the administration of the pharmaceutical compositions may be large enough to produce the desired effect, whereby, for example, autoreactive T cells are depleted, as measured by the seventh aspect of the present invention, is achieved, and the autoimmune disease is significantly prevented, suppressed, or treated. The doses may not be so large as to cause adverse side effects, such as unwanted cross reactions, generalized immunosuppression, anaphylactic reactions and the like.

The pharmaceutical compositions may further comprise suitable pharmaceutically acceptable carriers comprising excipients and auxiliaries which may facilitate processing of the active compositions into preparations which can be used pharmaceutically. Additives to the pharmaceutical compositions may include the inclusion of an adjuvant, such as alum, chitosan, or other adjuvants known in the art. (See, for example, Warren et al., Ann. Rev. Immunol. 4:369-388 (1986); Chedid, L., Feder. Proc. 45:2531-2560 (1986), which are incorporated herein by reference). The pharmaceutical compositions may also further comprise liposomes to enhance delivery or bioactivity, using methods and compounds known in the art.

Suitable formulations for parenteral administration include aqueous solutions of the inactivated autoreactive T cells, for example, water-soluble salts in aqueous solution. In addition, oil suspensions comprising inactivated autoreactive T cells may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. The suspension may also contain stabilizers.

The inactivated autoreactive T cells may be formulated using conventional pharmaceutically acceptable parenteral vehicles for administration by injection. These vehicles may be nontoxic and therapeutic, and a number of formulations are set forth in Remington's Pharmaceutical Sciences, (supra). Nonlimiting examples of excipients are water, saline, Ringer's solution, dextrose solution and Hank's balanced salt solution. Pharmaceutical compositions may also contain minor amounts of additives such as substances that maintain isotonicity, physiological pH, and stability.

The inactivated autoreactive T cells may be formulated at total cell concentrations including from about $5 \times 10^2$ cells/ml to about $1 \times 10^9$ cells/ml. Preferred doses of the inactivated autoreactive T cells for use in preventing, suppressing, or treating an autoimmune disease may be in the range of about $2 \times 10^6$ cells to about $9 \times 10^7$ cells.

8. Determination of TCR Repertoire

In an eleventh aspect, the present invention is drawn to a method of determining the repertoire of nucleic acids encoding one or more T cell receptors, or a portion thereof, in an autoimmune patient by amplifying nucleic acids encoding one or more T cell receptors from T cells isolated by the first or third aspects of the present invention, wherein said amplification is performed using a primer pair. The first primer of the primer pair may be an oligonucleotide of about 15 to 30 nucleotides in length that hybridizes to a nucleic acid comprising the variable region of the TCR gene. The second primer of the primer pair may be an oligonucleotide of about 15 to 30 nucleotides in length that hybridizes to a nucleic acid comprising the constant region of the TCR gene. The primer pair may be used to amplify a nucleic acid that hybridizes to the Vβ-Dβ-Jβ region of the TCR gene.

Nucleic acids encoding one or more T cell receptors from T cells (the "Target Sequence") or a fragment thereof may be amplified from a sample by the polymerase chain reaction (PCR) using any particular PCR technique or equipment known in the art. For example, PCR amplification may follow a procedure wherein a reaction mixture is prepared that contains the following ingredients: 5 μL 10×PCR buffer II (100 mM Tris-HCl, pH 8.3, 500 mM KCl), 3 μL 25 mM $MgCl_2$, 1 μL 10 mM dNTP mix, 0.3 μL Taq polymerase (5 U/μL) (AmpliTaq Gold, Perkin Elmer, Norwalk, Conn.), 30 pmol of a first primer, 30 pmol of a second primer, and 1 μL of sample DNA. The polymerase may be stable at temperatures of at least 95° C., have a processivity of 50-60 and have an extension rate of greater than 50 nucleotides per minute.

The PCR reaction may be performed with an amplification profile of 1 min at 95° C. (denaturation), 20 sec at 56° C. (annealing), and 40 sec at 72° C. (extension) for a total of 40 cycles. Before the first cycle begins, the reaction mixture may undergo an initial denaturation for a period of about 5 min to 15 min. Similarly, after the final cycle is complete, the reaction mixture may undergo a final extension for a period of about 5 min to 10 min. Certain PCR reactions may work with as few as 15 to 20 cycles or as many as 50 cycles. Depending upon the specific PCR reaction, longer or shorter incubation times and higher or lower temperatures for each step of the amplification profile may be used.

The sample comprising the Target Sequence, may be a nucleic acid, such as genomic DNA, cDNA, DNA previously amplified by PCR, or any other form of DNA. The sample may be isolated, directly or indirectly, from any animal or human tissue comprising T cells, such as peripheral blood mononuclear cells (PBMC). Genomic DNA may be isolated directly from a tissue comprising T cells. cDNA may be isolated indirectly by reverse transcription of mRNA directly isolated from a tissue comprising T cells.

The ability to detect the Target Sequence may be enhanced by isolating the sample DNA indirectly by amplification of genomic DNA, cDNA, or any other form of DNA, by a two-step PCR reaction. For example, a first PCR amplification reaction may be performed to amplify a preliminary fragment that is larger than, and comprises, a fragment to which the first and second primers are capable of selectively binding on opposite strands. A second PCR amplification reaction may then be performed, using the preliminary fragment as a template with the first and second primers, to amplify a fragment comprising the Target Sequence. If either the first or second primer is used in the first PCR reaction to amplify the preliminary fragment, the second PCR reaction is "semi-nested." If neither the first or second primer is used in the first PCR reaction to amplify the preliminary fragment, the second PCR reaction is "nested."

In an exemplary two-step PCR reaction, one or more nucleic acids encoding one or more T cell receptors from T cells may be amplified by performing a first PCR reaction using a first preliminary primer that anneals to the Vβ region of the TCR gene and a second preliminary primer that anneals to the Cβ region of the TCR gene, which amplifies a preliminary fragment that extends from Vβ through the Vβ-Dβ-Jβ junction to Cβ, followed by a second PCR reaction which may be nested or semi-nested. In light of the present disclosure, the skilled artisan will be able to select appropriate primers and reaction conditions for PCR amplification of the Target Sequence.

After amplification of the Target Sequence, the amplified product may be detected by a number of procedures. For example, an aliquot of amplification product may be loaded onto an electrophoresis gel, to which an electric field is applied to separate DNA molecules by size. In another method, an aliquot of amplification product may be loaded onto a gel stained with SYBR green, ethidium bromide, or another molecule that will bind to DNA and emit a detectable signal. A dried gel may contain a labeled oligonucleotide that hybridizes to the Target Sequence, from which an autoradiograph may be taken by exposing the gel to film.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Isolation of Myelin-Reactive T Cells for T Cell Vaccination

1. Preparation of PBMC and the Primary Stimulation

Fresh blood specimens from MS patients and control patients were processed within 2 hours of collection. Alternatively, mononuclear cells may be obtained from the cerebrospinal fluid (CSFMCs) of MS patients. Peripheral blood mononuclear cells (PBMCs) were isolated from the whole blood by standard Ficoll gradient separation method. Specifically, heparinized blood was diluted with Hanks balanced salt solution (HBSS) (1:1 blood/HBSS) and then slowly laid over the Ficoll-hypaque solution in a centrifuge tube and centrifuged for 20 minutes at 1800 rpm, 18° C. to 25° C., with no brake. PBMCs were then washed by adding excess HBSS and centrifuged at 1700 rpm for 10 minutes at 18° C. to 25° C. Purified PBMCs were washed three times in RPMI 1640 medium by centrifugation and subsequently resuspended in AIM V medium (Gibco, Grand Island, N.Y.). Cell number was counted and cells were plated onto 96-well U-bottomed culture plates at a density of 200,000 cells/well. All plates were labeled with patient number and patient initials. The cells were incubated at 37° C. in the presence of synthetic peptides listed in Table 1 corresponding to the known immunodominant regions of three myelin proteins, myelin basic protein (P), proteolipid protein (PLP), and myelin oligodendrocyte glycoprotein (MOG) at a concentration of 20 µg/ml. Plates were placed in a $CO_2$ incubator at 37° C. and visually inspected daily. Cells were cultured for 7-10 days without change of culture medium to selectively grow antigen-specific T cells.

TABLE 1

| | Activating Peptides | |
|---|---|---|
| Myelin Antigen Peptides | Amino Acid Sequences | |
| Myelin basic protein, peptide-1 (MBP-1) | ENPVVHFFKNIVTPRTP | SEQ ID NO.1 |
| Myelin basic protein, peptide-2 (MBP-2) | SKIFKLGGRDSRSGSPMARR | SEQ ID NO.2 |
| Proteolipid protein, peptide-3 (PLP-3) | LFCGCGHEALTGTEKLIETY | SEQ ID NO.3 |
| Proteolipid protein, peptide-4 (PLP-4) | WTTCQSIAFPSKTSASIGSL | SEQ ID NO.4 |
| Myelin oligodendrocyte glycoprotein, peptide-6 (MOG-6) | GQFRVIGPRHPIRALVG | SEQ ID NO.5 |
| Myelin oligodendrocyte glycoprotein, peptide-7 (MOG-7) | EVELPCRISPGKNATGMEVGW | SEQ ID NO.6 |

2. Identification and Selection of Antigen-Specific T Cells

The cells described above are then selected for the expression of gene products indicative of activated T cells. See Section 2(a) above. A Cytokine Catch Reagent (Miltenyi Biotec) (as described above) is used in order to detect the intracellular cytokine γIFN or TNFα when ultimately excreted from the cell. Briefly, the Cytokine Catch Reagent (typically a bispecific antibody which binds to both the activated T cell marker and the secreted cytokine) is incubated first with the cells at 4-8° C. in order to bind to the CD45 molecule on the cell surfaces or other activated T cell surface marker such as CD69. The cells with the bound Cytokine Catch Reagent are then incubated at 37° C. for 45 minutes to allow the γIFN or TNFα within the cell to also bind to the Cytokine Catch Reagent as the cytokine is secreted from inside the cell during this incubation period. γIFN or TNFα, now bound to the cell surface by the Cytokine Catch Reagent which is then detected using an antibody specific for cytokine of interest conjugated to the fluorochrome PE.

The cell surface molecules CD4 and CD69, are detected using antibodies conjugated to different fluorochromes. The CD4$^+$ cell population is selected first by gating and then, within this population, the "double-positive" (CD69 and IFNγ or CD69 and TNFα) stained cells are separated by FACS and collected aseptically.

The isolated myelin-reactive T cells are then directly expanded by stimulating with rIL-2, PHA, anti-CD3 or other general T cell mitogen in the presence of irradiated autologous PBMCs for 7-10 days. Myelin-reactive T cells lines are propagated in culture until the total cell number reached approximately 20 million.

EXAMPLE 2

Diagnosis of MS

Two to 100 ml of blood are collected from the patient and one or more synthetic peptides are added directly to the whole blood to prime, or stimulate, the T lymphocytes. The peptides correspond to the known immunodominant regions of three myelin proteins, myelin basic protein (MBP), proteolipid protein (PLP), and myelin oligodendrocyte glycoprotein (MOG). The blood is incubated with the peptides for 1 to 7 days to activate the myelin-specific T cells. At the end of this antigen-priming period, the cells are re-challenged with antigens in a short re-stimulation assay.

Figure 2:
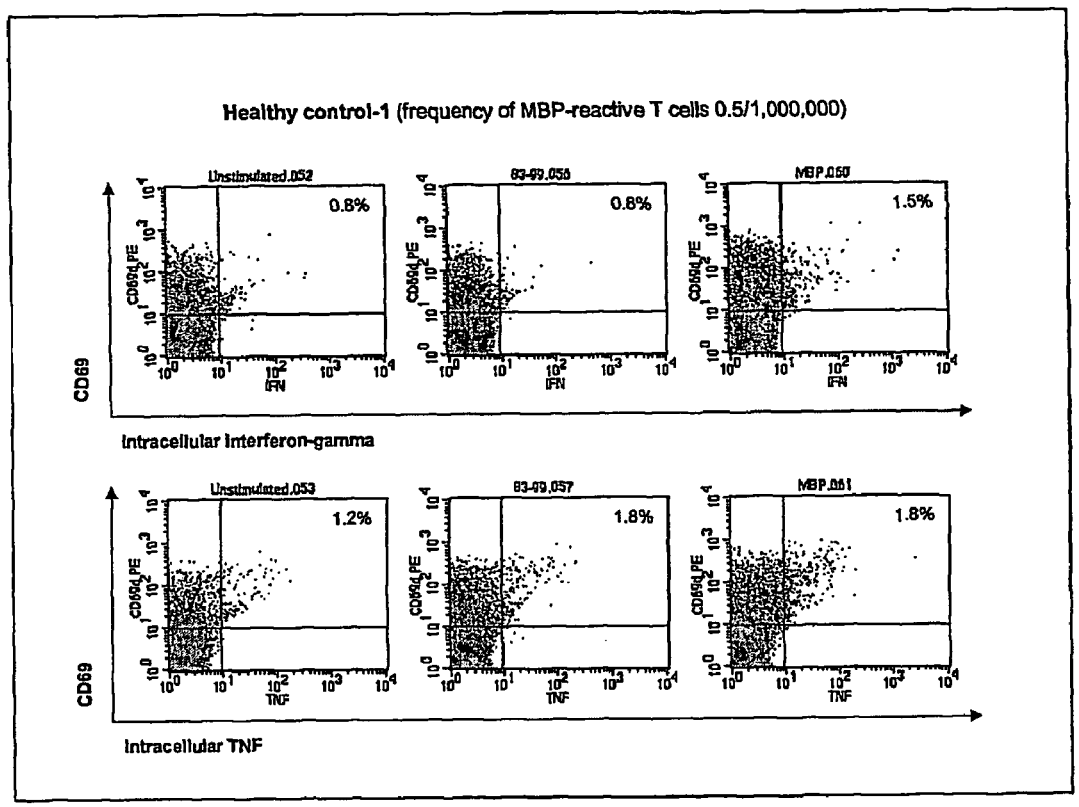
FIG. 2 demonstrates FACS identification of cells expressing CD69 and γIFN (top) and CD69 and TNFα (bottom) in a healthy control patient before stimulation (left), after stimulation with residues 83-99 of MBP (middle), and after stimulation with residues 83-99 of MBP (right).

Myelin peptide-activated T cells are detected by permeabilizing the cell membrane with a detergent solution, washing the cells, then incubating with one or more staining antibodies to detect CD4 or CD69 molecules on the cell surface or IFNγ or TNFα intracellularly. The staining antibodies are conjugated to different fluorochromes so that they fluoresce at different wavelengths when excited by a 488 nanometer laser by FASC analysis. The population of CD4$^+$ T cells is selected first by using the CD4$^+$ cells for gating and then within this population, the cells that are immunoreactive with both antibodies (CD69 and γIFN or CD69 and TNFα) are identified. This population of "double-positive" myelin-reactive T cells has been shown to increase significantly in multiple sclerosis (MS) patients as compared to healthy controls in a similar study (FIG. 1, MS patient, FIG. 2, healthy control). Using this method, the number of myelin-reactive T cells circulating in the blood of a patient may be determined before, during and after treatment to determine the effect of an MS therapy on the autoreactive T cell population. The endpoint may be determined as either the percentage of double-positive stained cells or as the absolute number of double-positive stained cells.

EXAMPLE 3

Diagnosis of MS Using Antibody-Conjugated Liposomes

Whole blood is obtained from a patient and stimulated with one or more synthetic peptides as described in Example 2. The blood is incubated with the peptides for 3 to 16 hours to activate the myelin-specific T cells. At the end of this antigen-priming period, the cells may be re-challenged with antigens in a short re-stimulation assay prior to staining with magnetofluorescent liposomes conjugated to antibodies against IFNγ, TNFα, or a combination thereof. The cells are also stained with an antibody to CD4 and/or CD69. The stained myelin-reactive T cells are detected as described in Example 2.

EXAMPLE 4

Determination of TCR Clonal Repertoire

The T cell receptor (TCR) clonal repertoire represented in a cell population may be analyzed by isolating out the double-positive stained cell population by cell sorting as described in Example 2 and Example 3. DNA is extracted from the isolated cells and used to perform quantitative polymerase chain reaction (PCR) assays using oligonucleotide primers specific for 25 known TCR variable beta chain (Vβ) gene families. This procedure yields information on the distribution of TCR Vβ gene usage and indicates the clonality of pathogenic T cell populations. This method may also be used to determine if clonal or epitopic shifting of the myelin-reactive T cell population is occurring in an MS patient.

EXAMPLE 5

The Depletion of Myelin-reactive T Cells by T Cell Vaccination

Patients with relapsing-remitting (RR)-MS and secondary-progressive (SP)-MS received three subcutaneous injections of irradiated autologous myelin-reactive T cell clones isolated by direct expansion, with three additional injections 4, 12 and 20 weeks thereafter. Patients were monitored for changes in the precursor frequency of myelin-reactive T cells, rate of relapse, expanded disability status score (EDSS) and MRI lesion activities over a period of 24 months. The results were compared with pre-vaccination values in a self-paired manner. In addition, the clinical data of the placebo arms of RR-MS in the beta-interferon-1a clinical trial (Jacobs et al., 1996) and SP-MS in a recent beta-IFN-1b study (European Study Group, Lancet, 352:1491-1497 (1998)) were included to provide natural history data of MS for comparison. The T cell frequency was either undetectable or substantially declined after vaccination at week 20. The results confirmed depletion of myelin-reactive T cells by T cell vaccination in patients with MS.

EXAMPLE 6

Vaccination of MS Patient Using Autologous Myelin-Reactive T Cells

The vaccination protocol is similar to that used in previous clinical studies (Zhang et al., 1993, Medaer et al., 1995). Briefly, myelin-reactive T cell clones prepared according to Example 1 are activated with phytohemagglutinin (PHA) (4 µg/ml) in the presence of irradiated PBMCs as a source of accessory cells. Cells are then cultured for 10 days in RPMI 1640 media supplemented with 10% heat-inactivated human AB serum and 100 units per mL of rIL-2. Activated myelin-reactive T cells are subsequently washed three times with sterile saline to remove residual PHA, rIL-2 and cell debris and finally resuspended in 2 ml of saline. After irradiation (10,000 rads, $^{137}$Ce source), the cells are injected subcutaneously on two arms (1 ml/arm). The number of T cells used for vaccination range from 40×10⁶ to 80×10⁶ cells per injection and are chosen by an extrapolation of T cell doses effective in experimental animals on the basis of relative skin surface areas (Ben-Nun et al., 1981). Each patient receives two subcutaneous injections followed by repeat injections at 4, 12 and 20 weeks.

Patients are then observed for time to onset of confirmed progression of disability, EDSS, rate of relapse and MRI lesion activities. The results are compared with the patient's own pre-treatment course as well as the placebo arms of two recent clinical trials in RR-MS and SP-MS patients, which serve as an estimate of the natural history of MS (Jacobs et al, 1996), European Study Group, 1998). Time to progression is determined by an increase of at least 1.0 on the EDSS (Poser et al., 1983) persisting for at least 2 months. On-study exacerbations are defined by the appearance of new neurological symptoms or worsening of preexisting neurological symptoms lasting for at least 48 hours, accompanied by objective change on neurological examination (worsening of at least 0.5 point on EDSS). Patients are instructed to report events between the scheduled regular visits, and are examined by a neurologist if symptoms suggested an exacerbation. Safety assessments included adverse events, vital signs and physical examinations at regular visits. The differences in the clinical variables in study patients before and after T cell vaccination are analyzed using the Wilcoxon's rank-sum test.

EXAMPLE 7

Alteration of Clinical Course of MS After Vaccination

Patients receive T-cell vaccinations prepared according to Example 1 with no adverse effects. The mean EDSS declines in patients with RR-MS over a period of 24 months after vaccination. By comparison, there is an increase of mean EDSS by 0.61 in the natural history of RR-MS (n=56) over the same period of observation, as was reported in a trial conducted using beta-IFN-1a trial (Jacobs et al., 1996). In addition, the proportion of the patients that have either unchanged or improved EDSS is higher than that of the natural MS history. Few, if any, patients in the treated RR-MS group progress beyond EDSS of 2.0 within 24 months as compared to 18% of patients in the natural history of MS.

In the SP-MS cohort, mean EDSS progresses slower over a period of 24 months as compared to +0.6 recorded in the natural history of SP-MS (European Study Group, Lancet 1998; 352:1491-1497). Furthermore, estimation of time to confirmed progression using the Kaplan-Meier method shows considerable delay as compared to the natural history of MS patients (20% progression in 12 months for RR-MS and 9 months for SP-MS) (Jacobs et al., Ann. Neurol, 1996; 39:285-294, European Study Group, 1998).

What is claimed is:

1. An autologous T-cell vaccine consisting of inactivated T cells that are reactive against SEQ ID NOS: 1-6.

2. An autologous T cell vaccine comprising inactivated T cells elicited from a patient sample comprising mononuclear cells by a combination of antigens consisting of SEQ ID NOS:1-6.

3. The T cell vaccine according to claim 1, wherein the T cells are inactivated by irradiation.

4. The T cell vaccine according to claim 2, wherein the T cells are inactivated by irradiation.

5. The T cell vaccine according to claim 2, wherein the patient sample comprises peripheral blood T cells.

6. The T cell vaccine according to claim 2 wherein the patient sample comprises cerebrospinal fluid T cells.

7. A method of treating multiple sclerosis comprising administering to a patient in need thereof the autologous T cell vaccine according to claim 1.

8. A method of treating multiple sclerosis comprising administering to a patient in need thereof the autologous T cell vaccine according to claim 2.

* * * * *